(12) United States Patent
Kawada et al.

(10) Patent No.: US 8,198,387 B2
(45) Date of Patent: Jun. 12, 2012

(54) PROTON-CONDUCTING COMPOUND AND PROTON-CONDUCTING POLYMER

(75) Inventors: Atsushi Kawada, Kitakyushu (JP); Aya Tashiro, Kitakyushu (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 274 days.

(21) Appl. No.: 12/312,031

(22) PCT Filed: Oct. 30, 2007

(86) PCT No.: PCT/JP2007/071072
§ 371 (c)(1),
(2), (4) Date: Apr. 23, 2009

(87) PCT Pub. No.: WO2008/053864
PCT Pub. Date: May 8, 2008

(65) Prior Publication Data
US 2010/0063249 A1    Mar. 11, 2010

(30) Foreign Application Priority Data

Oct. 30, 2006  (JP) .................................. 2006-293974
Dec. 28, 2006  (JP) .................................. 2006-354411
Dec. 28, 2006  (JP) .................................. 2006-354412

(51) Int. Cl.
*C08F 26/06* (2006.01)
*C07D 251/54* (2006.01)
(52) U.S. Cl. ........................................ 526/261; 544/196
(58) Field of Classification Search .................. 526/261; 544/196
See application file for complete search history.

(56) References Cited

U.S. PATENT DOCUMENTS 4,266,053 A * 5/1981 Imanaka et al. ............. 544/196
(Continued)

FOREIGN PATENT DOCUMENTS

JP          58-092614 A     6/1983
(Continued)

OTHER PUBLICATIONS

STN Structure search (Nov. 16, 2011).*
Dean M. Tigelaar et al., "Study of the incorporation of protic ionic liquids into hydrophilic and hydrophobic rigid-rod elastomeric polymers," Polymer 47 (2006) pp. 4269-4275.
(Continued)

*Primary Examiner* — David W Wu
*Assistant Examiner* — Vu A Nguyen
(74) *Attorney, Agent, or Firm* — Edwards Wildman Palmer LLP; James E. Armstrong, IV; Nicholas J. DiCeglie, Jr.

(57) ABSTRACT

Provided is a proton-conducting compound which provides proton conductivity without humidification and is suitable for electrochemical device materials such as solid electrolytes for fuel cells and electrolytes for batteries. Provided also is a proton-conducting polymer. The proton-conducting compound is composed of a melamine compound salt obtained from a melamine compound represented by the following formula (1) and a Bronsted acid and the proton-conducting polymer is obtained by homopolymerizing or copolymerizing the melamine compound salt. In formula (1), $R_1$, $R_2$, $R_3$, $R_4$, and $R_5$ each is independently an alkyl group, an aryl group, an alkenyl group, a heterocyclic group, or a hydrogen atom; at least one of them is a group other than hydrogen; $R_2$ and $R_3$ or $R_4$ and $R_5$ may join together to form a heterocyclic structure; and the alkyl group, the aryl group, the alkenyl group, or the heterocyclic group may have a substituent. A melamine compound salt wherein $R_1$ is $CH_2=CR_6-CO-O(CH_2)_n-$ polymerizes to yield a proton-conducting polymer. In this particular $R_1$ group, $R_6$ is hydrogen or an alkyl group and n is an integer equal to or larger than 1.

(1)

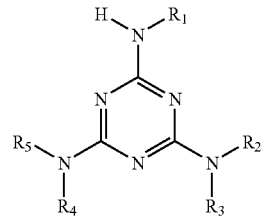

8 Claims, 6 Drawing Sheets

U.S. PATENT DOCUMENTS 5,182,388 A * 1/1993 Cipolli et al. .............. 544/195
5,677,450 A * 10/1997 Suzuki et al. .............. 544/194

FOREIGN PATENT DOCUMENTS

| JP | 2000-191729 A | 7/2000 |
|---|---|---|
| WO | WO-2005/085181 A1 | 9/2005 |

OTHER PUBLICATIONS

Supplemental European Search Report dated Mar. 16, 2010, issued on the corresponding European Patent Application No. 07830806.1.
International Search Report dated Jan. 8, 2008, issued on PCT/JP2007/071072.

* cited by examiner

[Fig. 1]
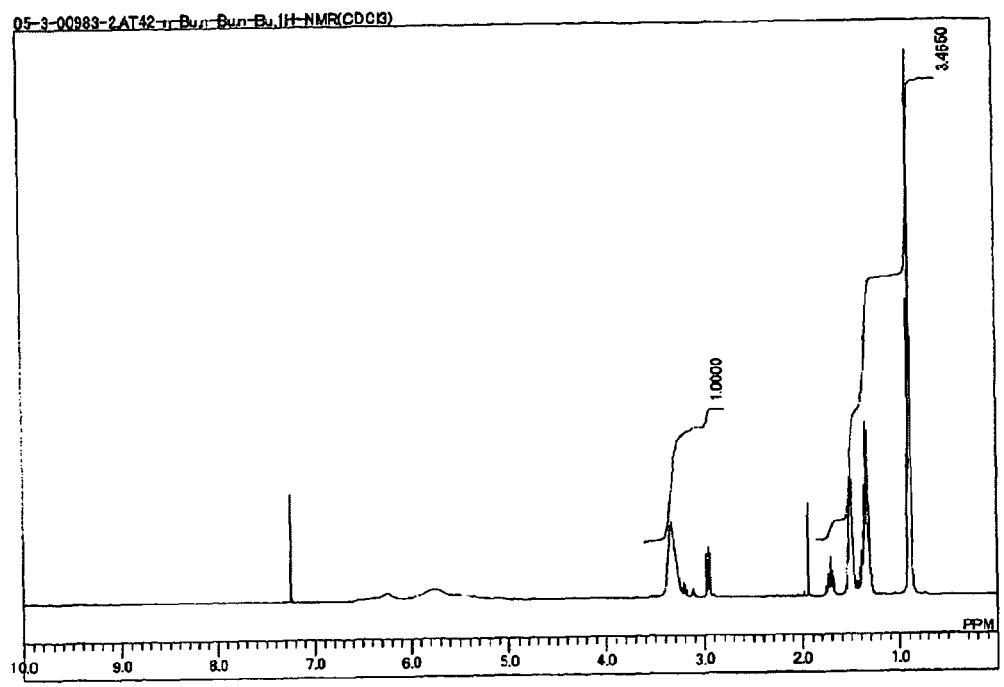
[Fig. 2]
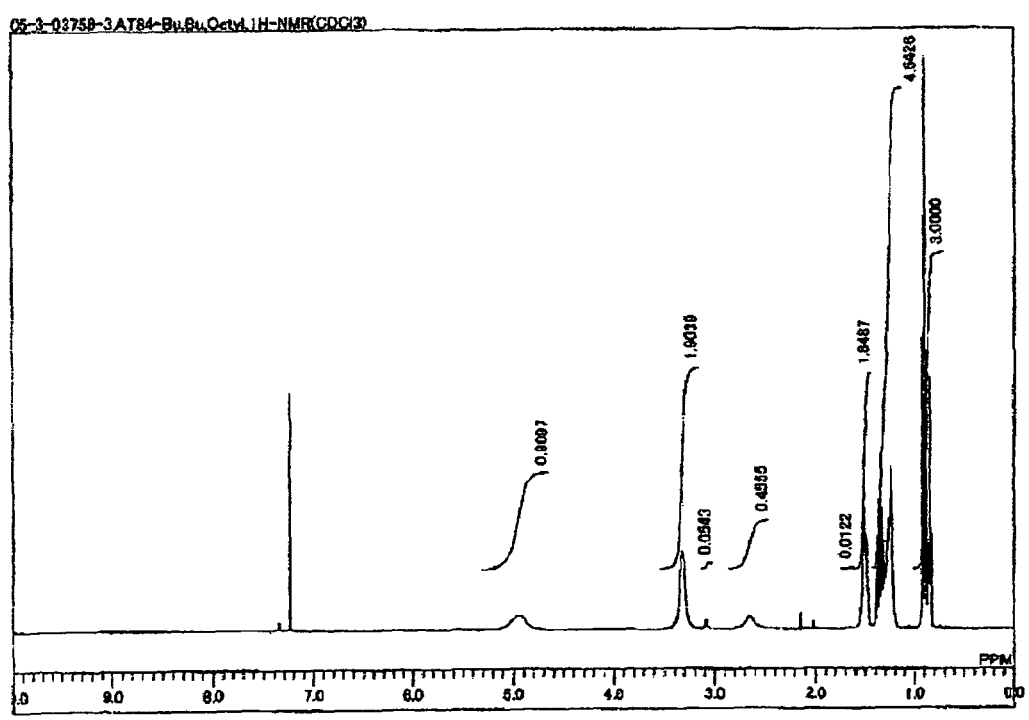

[Fig. 3]
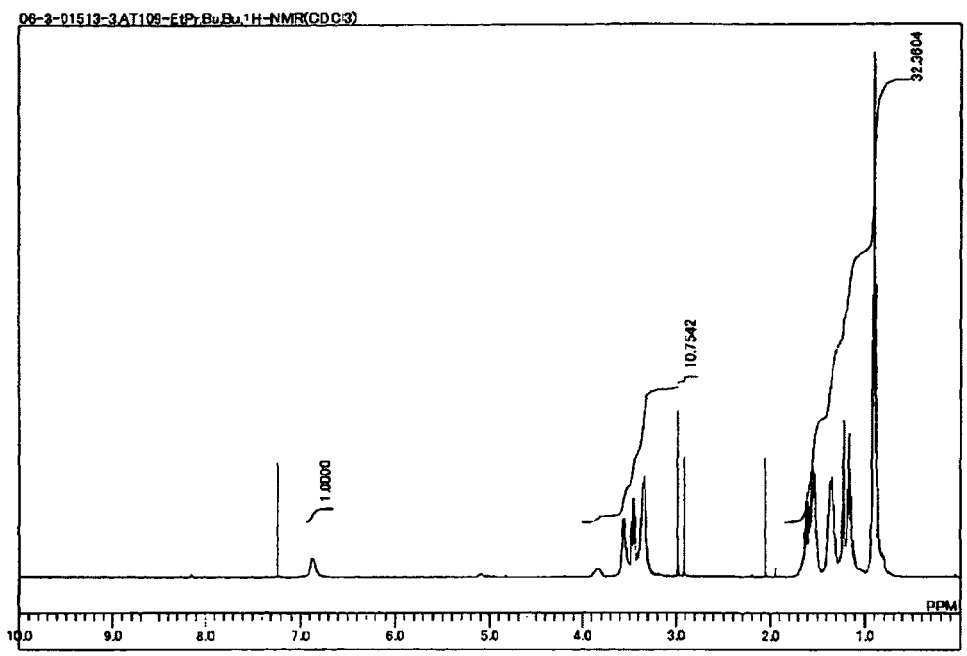
[Fig. 4]
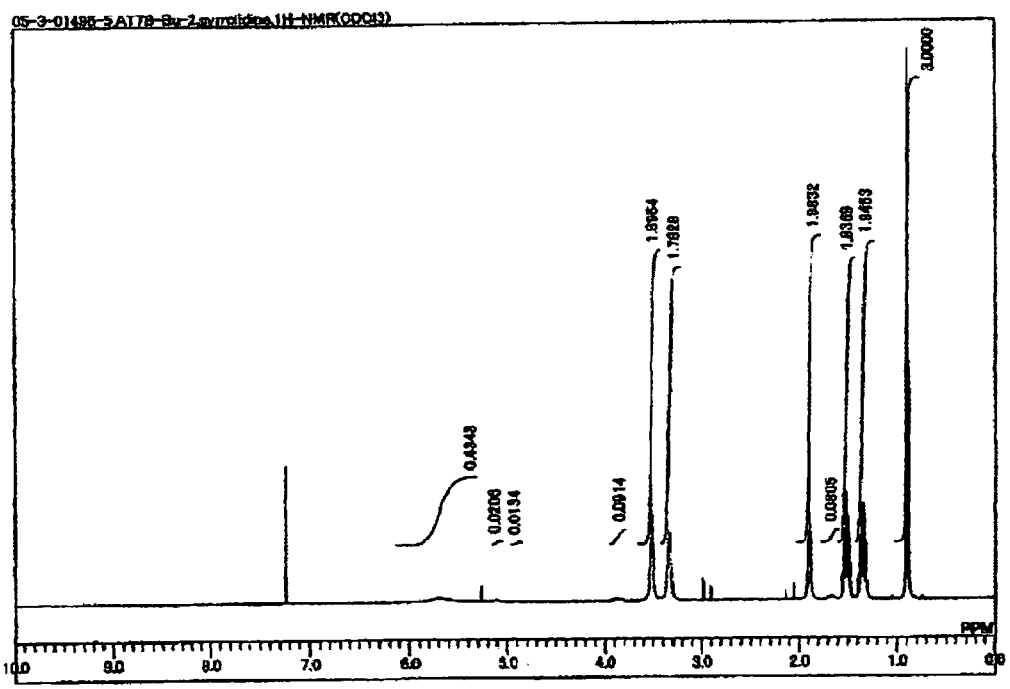

[Fig. 5]
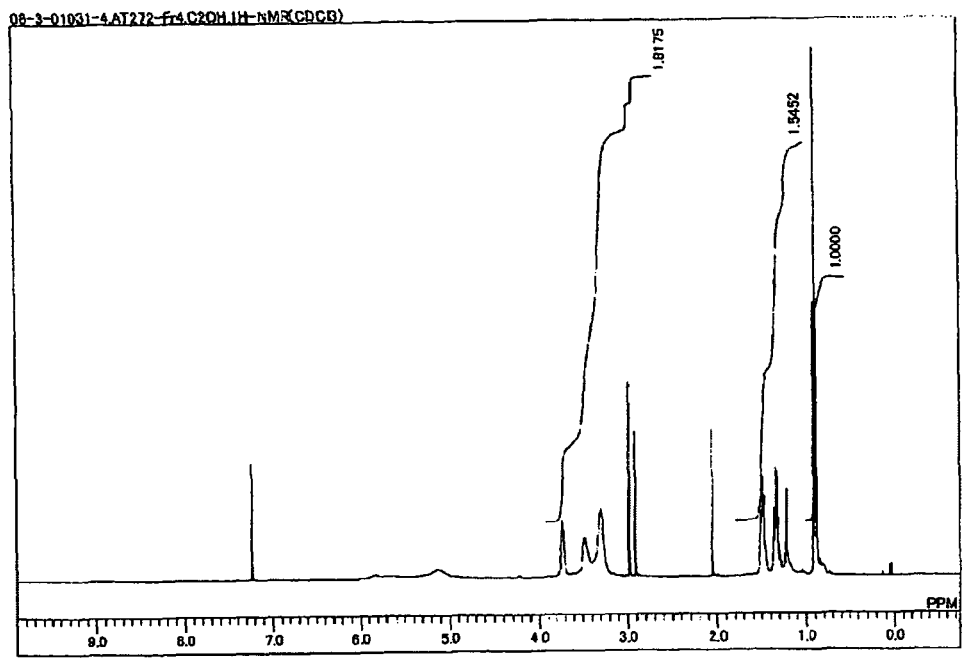
[Fig. 6]
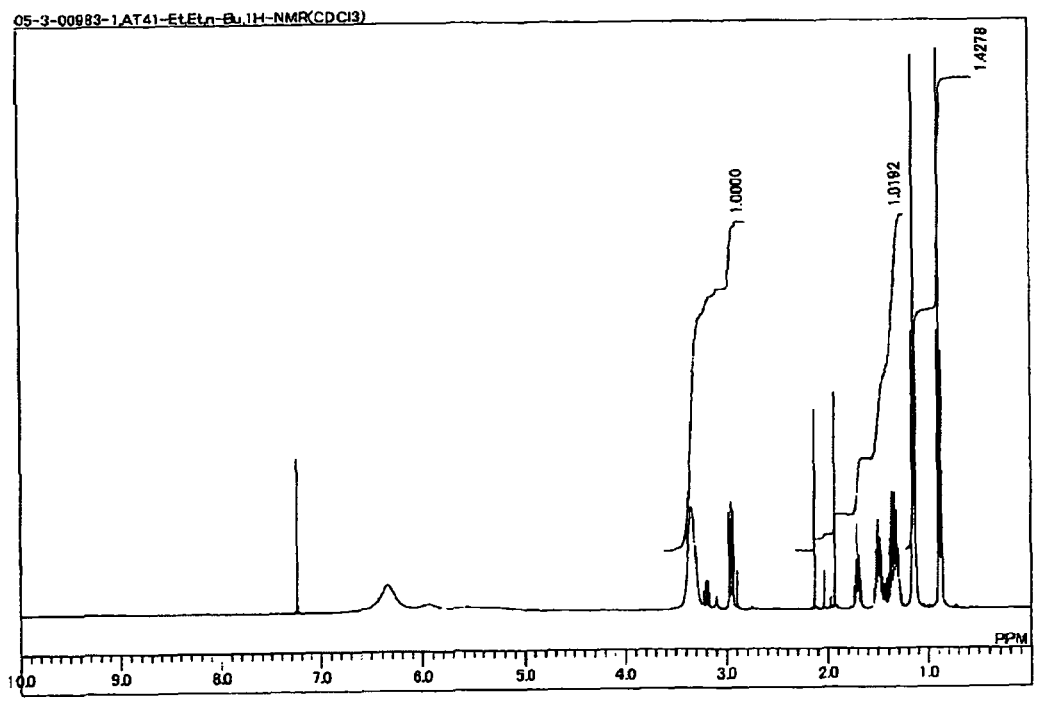

[Fig. 7]
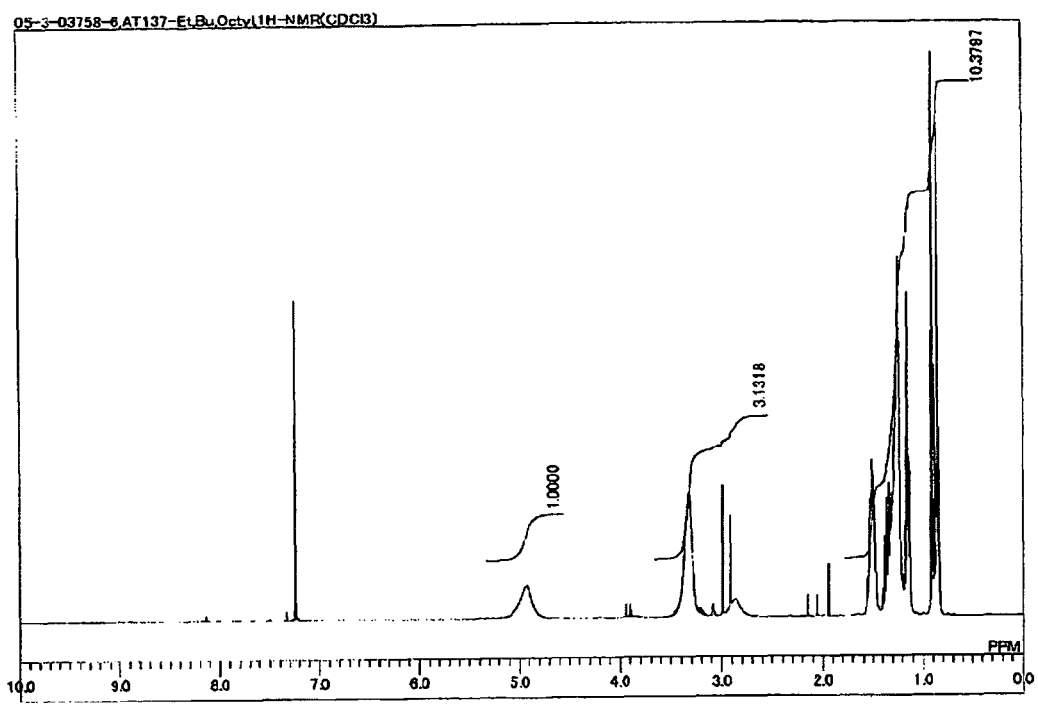
[Fig. 8]
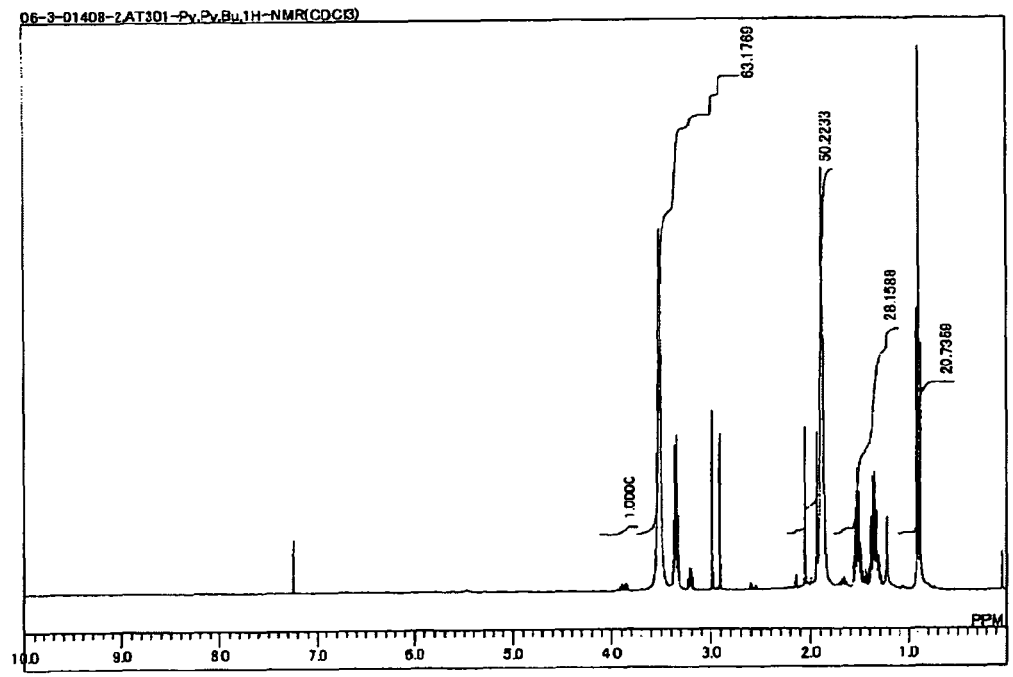

[Fig. 9]
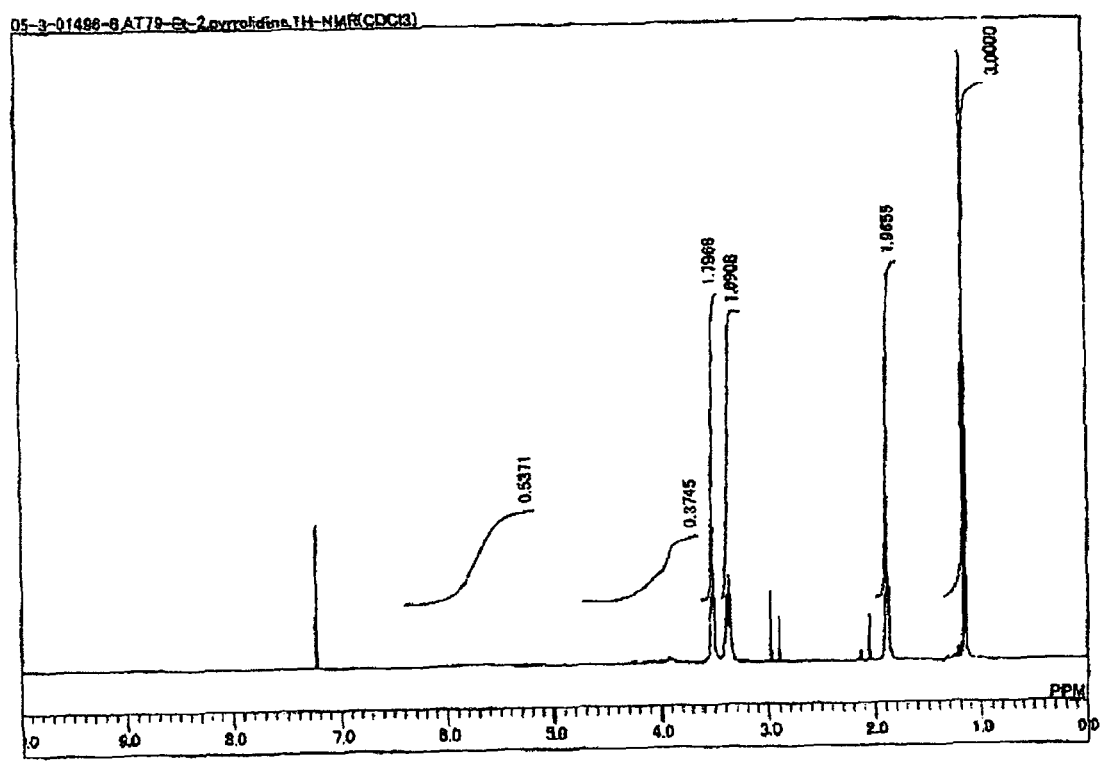
[Fig. 10]
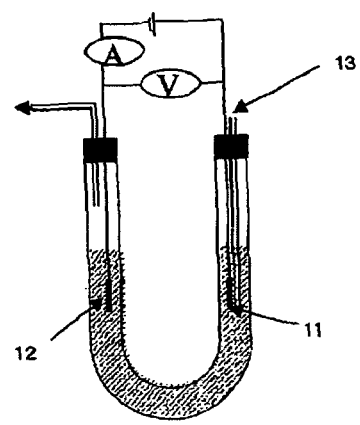

[Fig. 11]
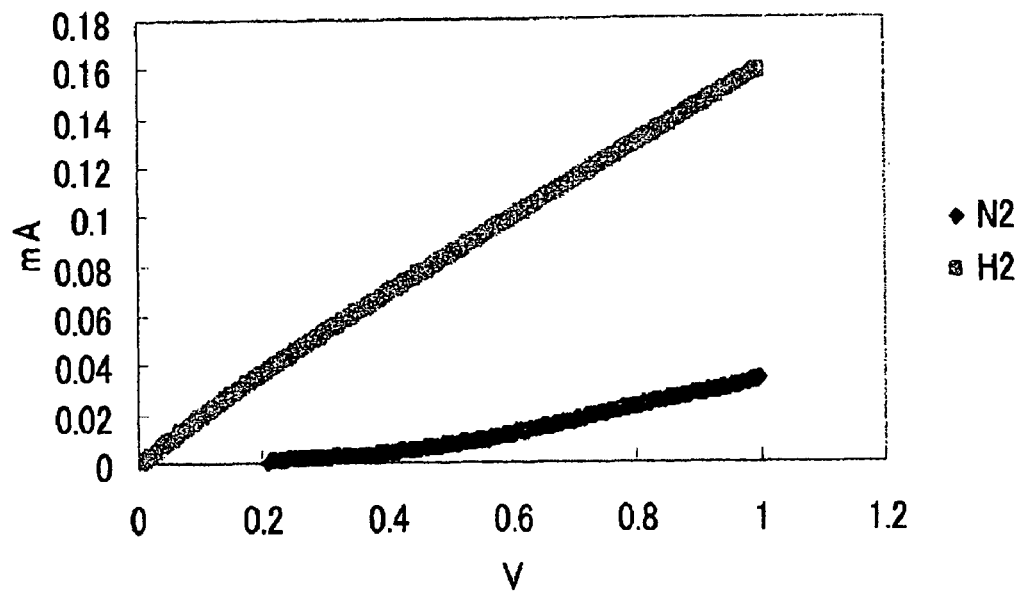
[Fig. 12]
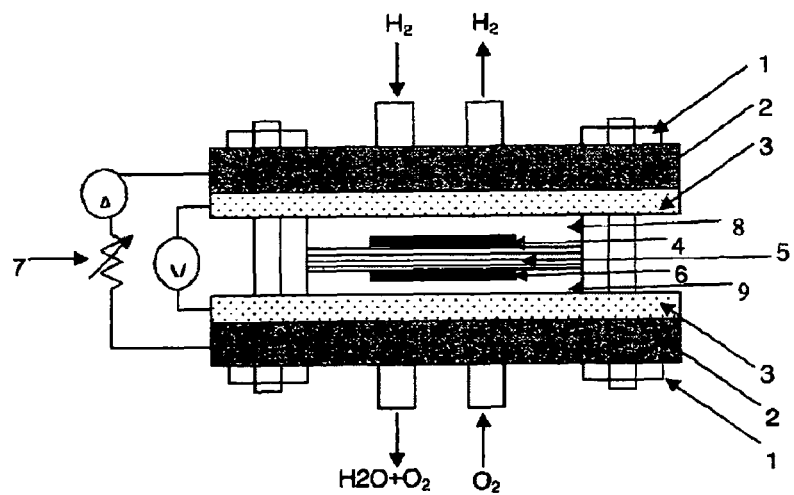

PROTON-CONDUCTING COMPOUND AND PROTON-CONDUCTING POLYMER

TECHNICAL FIELD

This invention relates to a novel proton-conducting compound that functions without humidification and to a polymer thereof. More particularly, this invention relates to a melamine derivative which is useful for a proton exchange material applicable to electrochemical devices related to battery and electrolysis and to a polymer thereof.

BACKGROUND TECHNOLOGY

A perfluorocarbonsulfonic acid membrane has been one of the electrolyte membranes used in the conventional solid polymer electrolyte membrane fuel cells (patent document 1). However, the perfluorocarbonsulfonic acid membrane, to its disadvantage, cannot be used in a dry condition as water contained in the membrane forms a proton-conducting path (non-patent document 1). Various membranes including the following have been tested for their capability of enhancing the proton conductivity in a dry condition: silica dispersion perfluorosulfonic acid membranes (patent document 2); inorganic-organic composite membranes (patent document 3); and phosphoric acid-doped graft membranes (patent document 4). However, all of the aforementioned membranes essentially require the presence of water in them for manifestation of proton conductivity and they have not offered a substantial solution to the problem of providing proton conductivity without humidification.

Thus, there is a growing demand for the development of proton conductors that do not require water and one of the proposed approaches is utilization of ionic liquids. The "ionic liquid" is a general term used for compounds that consist of a combination of an anion and a cation and melt below 100° C. It is advocated that an ionic liquid with a combination of ions tailored to a particular application can manifest the required properties (non-patent document 1). The applications proposed for ionic liquids include reaction solvents, electrolytes for batteries, lubricants, and heat transfer media.

Several proposals have been made on proton exchange materials mainly intended for use in fuel cells: for example, the use of aprotic ionic liquids composed of nitrogen-containing quaternary salts such as quaternary ammonium salts, quaternary pyridinium salts, and quaternary imidazolium salts and polymer materials having ion exchange groups in proton exchange membranes (patent documents 5-7) and the use of protic ionic liquids composed of imidazole compounds in proton exchange liquids and membranes (patent documents 8-13). However, the proton conductivity cited in the examples was in the range of $10^{-4}$ to $10^{-3}$ S/cm at most without humidification and this necessitated a further improvement for utilization as a proton exchange membrane without humidification. A proton exchange liquid or membrane obtained by using an imidazole-based ionic liquid containing a hydrogen fluoride-based compound as an anion is proposed as a material of high proton conductivity; however, the use of this material would pose a problem in the treatment of hydrogen fluoride.

Several proposals have also been made on proton-conducting solid electrolytes mainly intended for use in fuel cells: for example, the use of aprotic ionic liquids composed of nitrogen-containing quaternary salts such as quaternary ammonium salts, quaternary pyridinium salts, and quaternary imidazolium salts and polymer materials having ion exchange groups in proton exchange membranes (patent documents 5-6) and the use of protic ionic liquids composed of imidazole compounds in proton exchange liquids and membranes (patent documents 7-12). However, the proton conductivity of these materials shown in the examples was in the range of $10^{-4}$ to $10^{-3}$ S/cm without humidification and this necessitated a further improvement for utilization as a proton exchange material without humidification. Furthermore, all of the reported materials are prepared by impregnating a polymer material with an ionic liquid and a problem latent in these materials is leakage of the ionic liquid. To solve this problem, studies are in progress to develop solid electrolytes by increasing the molar mass of an ionic liquid. For example, the polymerization of an N-vinylimidazole salt, which is a protic ionic liquid, is known (patent document 13); however, the proton conductivity of the resulting polymer was not at a satisfactory level and needed to be improved further.

In spite of the advocacy described earlier that an ionic liquid with a combination of ions tailored to a particular application can manifest the required properties, quaternary imidazolium ions, alicyclic quaternary ammonium ions, quaternary alkylammonium ions, and the like are used in the majority of developmental works currently underway and it has been considered necessary to search for ions of a novel skeleton to make a breakthrough.

Accordingly, the inventors of this invention have made a search for novel skeletons in their studies aimed at ion-conducting materials and noted a singularity of chemical structure possessed by melamine compounds, namely, 1) a non-localized structure of electrons and 2) a high content of atoms capable of capturing protons, typically nitrogen atoms, in the skeleton. However, melamine compounds have been used so far as raw materials of pharmaceuticals and melamine resins and as additives to polymer materials and their use as an ion-conducting material has been known only in the patent document 15. This document discloses the proton conductivity of a mixture of unsubstituted melamine, cyanuric chloride, and p-toluenesulfonic acid, but it did not reach a practically useful level.

Patent document 1: JP7-90111 A
Patent document 2: JP6-111827 A
Patent document 3: JP2000-90946 A
Patent document 4: JP2001-213987 A
Patent document 5: JP2003-257484 A
Patent document 6: JP2004-31307 A
Patent document 7: JP2004-311212 A
Patent document 8: JP2006-32181 A
Patent document 9: JP-2006-32213 A
Patent document 10: JP2005-44550 A
Patent document 11: JP2005-44548 A
Patent document 12: WO2003-083981 A
Patent document 13: JP2005-174911 A
Patent document 14: JP2005-251466 A
Patent document 15: JP6-145642 A
Non-patent document 1: Chem. & Eng. News, May 15, 2000

DISCLOSURE OF THE INVENTION

Problems to be Solved by the Invention

An object of this invention is to provide a melamine-based proton-conducting compound that is capable of conducting protons without humidification. Another object of this invention is to provide a solid electrolyte that is capable of conducting protons without humidification or under a condition of low humidification (at 100° C. or above, at an Rh of 60% or less).

Means to Solve the Problems

The inventors have conducted extensive studies to solve the aforementioned problems, found that a melamine compound salt obtained from a specific melamine compound and a Bronsted acid shows high proton conductivity and a polymer produced by the polymerization of the said salt functions as a proton-conducting solid electrolyte with high proton conductivity, and completed this invention.

This invention relates to a proton-conducting compound composed of a melamine compound salt obtained from a melamine compound represented by the following formula (1) and a Bronsted acid:

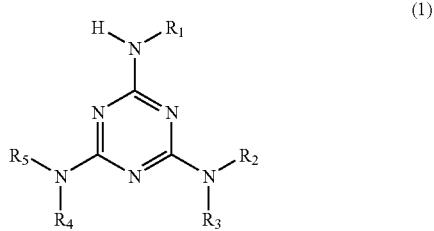

in formula (1), $R_1$, $R_2$, $R_3$, $R_4$, and $R_5$ each is independently an alkyl group, an aryl group, an alkenyl group, a heterocyclic group, or hydrogen and at least one of them is an alkyl group, an aryl group, an alkenyl group, or a heterocyclic group; $R_1$ and $R_2$ or $R_3$ and $R_4$ may join together to form a heterocyclic structure; and the alkyl group, the aryl group, the alkenyl group, or the heterocyclic group may have a substituent.

In the case where $R_1$ in formula (1) is a substituted alkyl group, $R_1$ is preferably $CH_2=CR_6—CO—O(CH_2)_n—$ for the purpose of producing a polymer. Here, $R_6$ is hydrogen or an alkyl group and n is an integer equal to or larger than 1.

Further, this invention relates to a proton-conducting polymer composed of a polymer produced by the polymerization of a melamine compound salt obtained from a melamine compound represented by the following formula (2) and a Bronsted acid:

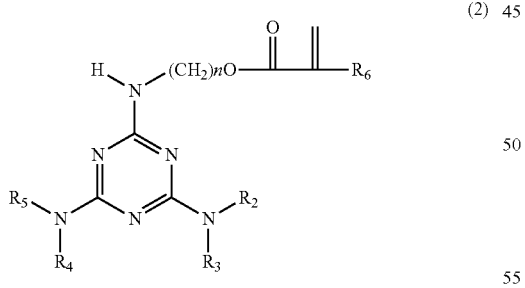

in formula (2), $R_2$, $R_3$, $R_4$, and $R_5$ each is independently an alkyl group, an aryl group, an alkenyl group, a heterocyclic group, or hydrogen and at least one of them is an alkyl group, an aryl group, an alkenyl group, or a heterocyclic group; $R_2$ and $R_3$ or $R_4$ and $R_5$ may join together to form a heterocyclic structure; the alkyl group, the aryl group, the alkenyl group, or the heterocyclic group may have a substituent; and $R_6$ is hydrogen or an alkyl group and n is an integer equal to or larger than 1.

It is preferable that the polymer here is produced by the copolymerization of a melamine compound salt and a crosslinking agent having two or more radically polymerizable functional groups that are radically copolymerizable with the said melamine compound salt; in this case, the amount of the crosslinking agent to be used is 0.1 to 50 wt % of the sum of the melamine compound salt and the crosslinking agent, and the crosslinking agent is an acrylic acid derivative having two or more radically polymerizable functional groups. It is further preferable that $R_2$ is hydrogen or both $R_2$ and $R_4$ are hydrogen in formulas (1) and (2) or that the melamine compound salt is obtained by reacting a melamine compound represented by formula (1) or (2) with a Bronsted acid in an equimolar ratio.

Further, this invention relates to a method for producing the aforementioned proton-conducting polymer which comprises treating a triazine compound represented by the following formula (3) with an aminoalcohol to give a melamine derivative represented by the following formula (4), treating the melamine derivative with an acrylic acid derivative represented by the following formula (5) to give a melamine compound represented by the aforementioned formula (2), reacting the melamine compound with a Bronsted acid to give a melamine compound salt, and polymerizing the melamine compound salt.

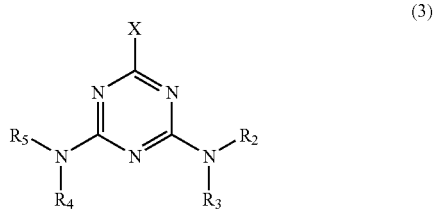

In formula (3), X is a halogen atom and $R_2$, $R_3$, $R_4$, and $R_5$ have the same meaning as in formula (2).

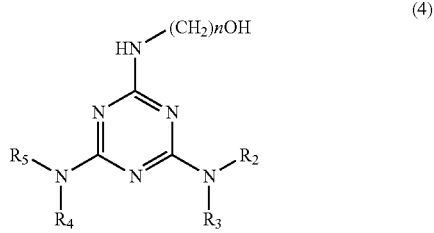

In formula (4), n is an integer equal to or larger than 1 and $R_2$, $R_3$, $R_4$, and $R_5$ have the same meaning as in formula (3).

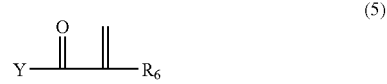

In formula (5), Y is an alkoxy group, a hydroxyl group, or a halogen atom and $R_6$ is hydrogen or an alkyl group.

The aforementioned proton-conducting compound or proton-conducting polymer serves as a proton exchange material. Further, this invention relates to a proton-conducting solid electrolyte comprising the aforementioned proton-conducting compound or proton-conducting polymer. The aforementioned proton-conducting compound or proton-conducting polymer may constitute a sole component or an effective component of the proton exchange material or proton-conducting solid electrolyte. When a proton-conducting solid electrolyte comprises a proton-conducting polymer as an effective component, the content of the said proton-conducting polymer is preferably 1 to 80 wt % of the electrolyte. Further, it is allowable for the electrolyte to contain 20 to 99 wt % of a thermoplastic polymer in addition to the proton-conducting polymer.

Further, this invention relates to a proton exchange material in which the aforementioned proton-conducting compound or proton-conducting polymer is held in a polymeric gelling agent. This proton exchange material can be molded into a proton exchange membrane.

Further, this invention relates to an electrolyte for electrochemical cells comprising the aforementioned proton-conducting solid electrolyte. Still further, this invention relates to a fuel cell comprising the aforementioned electrolyte for electrochemical cells or proton-conducting solid electrolyte membrane.

This invention will be described in more detail below.

The melamine compounds to be used in this invention are represented by the aforementioned formula (1) or (2). In formula (1), at least one of $R_1$ to $R_5$ is an alkyl group, an aryl group, an alkenyl group, or a heterocyclic group and others may be hydrogen. The alkyl group, the heterocyclic group, the alkenyl group, and the aryl group may have a substituent. Preferable examples of these groups are alkyl groups of 1 to 12 carbon atoms, six-membered aromatic hydrocarbon groups, alkenyl groups of 2 to 6 carbon atoms, and five- or six-membered heterocyclic groups (they may be aromatic heterocyclic groups). Examples of the hetero atom in the heterocyclic groups are nitrogen, oxygen, and sulfur and the number of hetero atoms in the heterocyclic ring is preferably 1 to 3. When $R_1$ is an alkyl group having a substituent, it may be $CH_2=CR_6-CO-O(CH_2)_n-$. In this case, the compound is a melamine compound represented by formula (2). Here, $R_6$ is hydrogen or an alkyl group and n is an integer of 1 or greater.

Examples of preferable substituents include alkyl groups of 1 to 6 carbon atoms, aryl groups of 6 to 12 carbon atoms, heterocyclic groups, an amino group, alkylamino groups of 1 to 6 carbon atoms, a nitro group, a carboxyl group, acyl groups of 1 to 6 carbon atoms, acyloxy groups of 1 to 6 carbon atoms, a cyano group, alkylsulfonyl groups of 1 to 6 carbon atoms, alkylsulfonyloxy groups of 1 to 6 carbon atoms, a sulfoxide group, a sulfonic acid group, alkoxycarbonyl groups of 1 to 6 carbon atoms, aryloxycarbonyl groups of 6 to 12 carbon atoms, aryloxy groups of 6 to 12 carbon atoms, alkenyl groups of 2 to 6 carbon atoms, alkynyl groups of 2 to 6 carbon atoms, and halogen atoms.

When any of $R_1$ to $R_5$ is an alkyl group or an alkenyl group, preferable substituents include a hydroxyl group and alkoxy groups of 1 to 6 carbon atoms. When any of $R_1$ to $R_5$ is an aryl group or a heterocyclic group, preferable substituents include alkyl groups of 1 to 6 carbon atoms, a hydroxyl group, and alkoxy group of 1 to 6 carbon atoms.

Furthermore, any two of $R_1$ to $R_5$ located adjacently may join together to form a cyclic structure: that is, $R_2$ and $R_3$ or $R_4$ and $R_5$ may join together to form a nitrogen-containing heterocyclic structure. In this case, the resulting heterocyclic compound is bound to have the skeleton of, for example, pyrrolidine, piperidine, or morpholine. This heterocyclic structure may be an aromatic heterocyclic structure and, further, it may have a substituent. The preferable heterocyclic structures are those of Compounds 3, 8, 19, and 26 to be described later.

The substituents for the aforementioned heterocyclic compounds preferably include those substituents that are cited above for $R_1$ to $R_5$; more preferably, they include a hydroxyl group, alkyl groups of 1 to 6 carbon atoms, and alkoxy groups of 1 to 6 carbon atoms.

The proton-conducting polymer of this invention is composed of a polymer produced by the polymerization of a melamine compound salt obtained from a melamine compound represented by the aforementioned formula (2) and a Bronsted acid.

In formula (2), $R_2$, $R_3$, $R_4$ and $R_5$ each means the same as in the aforementioned formula (1). Therefore, formula (1) is in common with formula (2) except when $R_1$ is represented by the aforementioned $CH_2=CR_6-CO-O(CH_2)_n-$.

The proton-conducting compound of this invention comprises a melamine compound salt obtained by treating a melamine compound represented by the aforementioned formula (1) with a Bronsted acid. The proton-conducting polymer of this invention is composed of a polymer produced by the polymerization of a melamine compound salt obtained from a melamine compound represented by the aforementioned formula (2) and a Bronsted acid. The proton-conducting compound is in common with the proton-conducting polymer in that they involve the formation of a melamine compound salt. The melamine compound salt obtained from a melamine compound represented by formula (1) or (2) and a Bronsted acid is hereinafter referred to as an M-B salt.

A Bronsted acid to be submitted to the reaction with a melamine compound represented by formula (1) or (2) may be an organic Bronsted acid or an inorganic Bronsted acid. The inorganic Bronsted acids include sulfuric acid, phosphoric acid, boric acid, and heteropolyacids. The organic Bronsted acids include carboxylic acids such as acetic acid, formic acid, and trifluoroacetic acid, alkylsulfonic acids such as methanesulfonic acid, ethanesulfonic acid, and octanesulfonic acid, fluorine-containing alkylsulfonic acids such as trifluoromethanesulfonic acid, perfluorobutanesulfonic acid, and perfluorooctanesulfonic acid, and fluorine-containing alkylsulfonic acid imides (hereinafter referred to as imide acids) such as bis(trifluoromethanesulfonyl)imide. Preferred are alkylsulfonic acids, fluorine-containing alkylsulfonic acids, alkylcarboxylic acids (RCOOH), and imide acids; the alkyl moiety in these acids contains 1 to 6 carbon atoms.

A melamine compound represented by formula (1) or (2) acts as a base and it is neutralized by a Bronsted acid to yield an M-B salt. Concretely, this neutralization is effected by any of generally known methods for the neutralization of an acid with a base. As one mole of a melamine compound represented by formula (1) or (2) is counted as one equivalent of a base, one equivalent of a Bronsted acid is required to effect the neutralization at an acid to base ratio of 1:1. However, it is possible to use an excess of one or the other. In such a case, it is preferable to use 0.5 to 2 equivalents of Bronsted acid per 1 mole of melamine compound. The salt obtained by using 1 equivalent of Bronsted acid per 1 mole of melamine compound shows a high concentration of M-B salt and performs excellently as a proton exchange material.

The procedure for the neutralization reaction consists of dissolving a melamine compound represented by formula (1) or (2) and a Bronsted acid in a solvent or mixing them in a solvent and allowing them to react.

For example, N,N',N"-tributyl-[1,3,5]triazine-2,4,6-triamine as a melamine compound and bis(trifluoromethanesulfonyl)imide as a Bronsted acid in an equimolar ratio are allowed to react in methanol to give the bis(trifluoromethanesulfonyl)imide salt of N,N',N"-tributyl-[1,3,5]triazine-2,4,6-triamine expressed by formula (6).

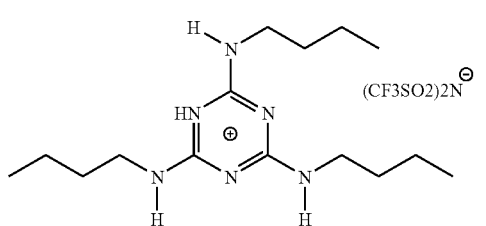

(6)

Likewise, a melamine compound represented by formula (2) and a Bronsted acid are dissolved or mixed in a solvent and allowed to react to give an M-B salt. For example, the compound expressed by formula (7) as a melamine compound and bis(trifluoromethanesulfonyl)imide as a Bronsted acid in an equimolar ratio are allowed to react in methanol to give the corresponding bis(trifluoromethanesulfonyl)imide salt.

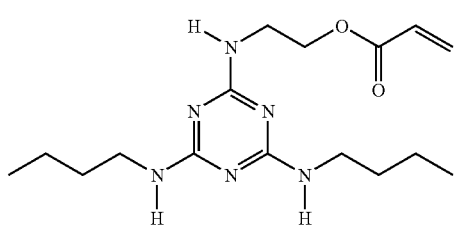

(7)

An M-B salt is a proton-conducting compound and is capable of exchanging protons even by itself; hence, it is useful as a proton exchange material or a proton-conducting solid electrolyte and it can also be used as an effective component thereof.

A proton exchange material is used in the form of a liquid or a solid. When an M-B salt is liquid at its service temperature, it may be used as it is or it may be compounded with other components and used. When an M-B salt is solid at its service temperature, it may be dissolved in a suitable solvent and used. The solvent here is not limited and any solvent that has a boiling point higher than the service temperature of the chosen M-B salt and dissolves the said salt without adversely affecting the proton conductivity can be used; for example, water, methanol as a representative of alcohols, toluene as a representative of aromatic hydrocarbons, hexane as a representative of aliphatic hydrocarbons, and dimethylformamide, dimethylacetamide, dimethylimidazolidinone, N-methylpyrrolidone, and dimethyl sulfoxide as representatives of aprotic polar solvents.

When a proton exchange material or a proton-conducting solid electrolyte is used in the form of a solid, the chosen M-B salt can be used as it is when it is solid at its service temperature. For example, an M-B salt of this kind can be used as a solid electrolyte without a solvent.

Moreover, a composite produced by compounding a polymeric gelling material and an M-B salt provides a proton exchange material according to this invention. In this case, the composite can be used as a polymer gel electrolyte. The method for producing a composite of this kind consists of adding a polymer, examples of which are described below, directly to an M-B salt, melting the mixture by heating, and then cooling or mixing the two in a suitable organic solvent, molding the mixture, and drying the molded article under reduced pressure to distil off the solvent. The polymer is not limited and any polymer that can hold the M-B salt in the solid form can be used. Examples of the polymer include vinyl polymers such as polyvinyl chloride, polyacrylonitrile, poly(methyl methacrylate), and polyvinylidene fluoride, polyethers such as polyoxymethylene, polyethylene oxide, and polypropylene oxide, polyamides such as nylon 6 and nylon 66, polyesters such as polyethylene terephthalate, and polycarbonates. It is possible to produce a composite by crosslinking of the polymerizable precursors of these polymers, for example, a polymerizable compound such as an acrylate. It is also possible to produce a composite by polymerizing a monomer in a solution containing an M-B salt.

A melamine compound represented by formula (1) can be produced easily in accordance with a known method; for example, the following sequence of reactions described in J. Am. Chem. Soc., 2002, 123, 8914-8922 can be used.

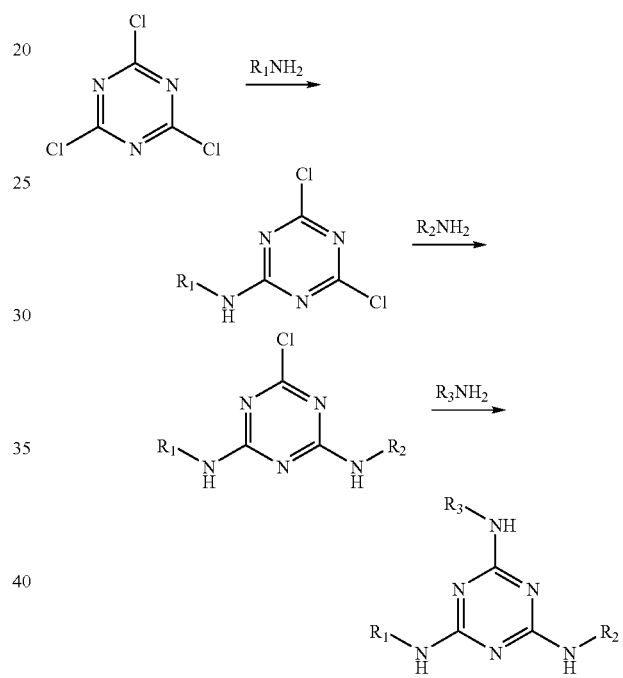

Preferable examples of the melamine compounds represented by formula (1) are shown below, but are not limited thereto. The number given below the chemical formula is the compound number.

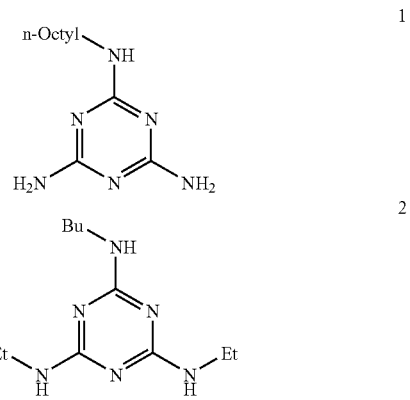

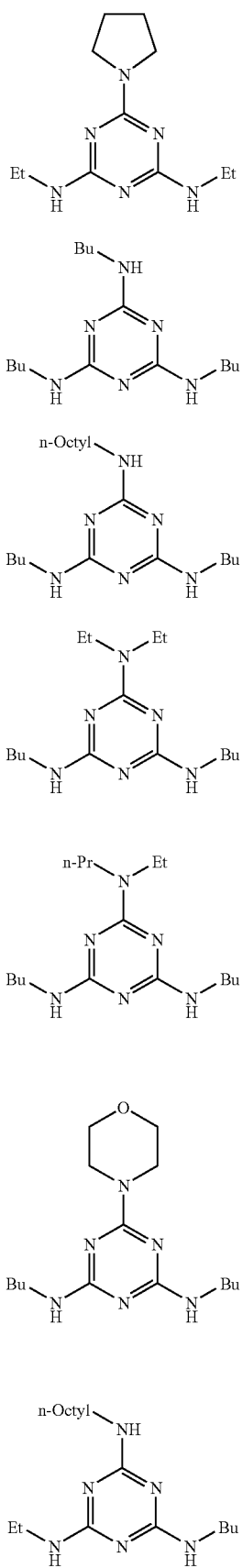
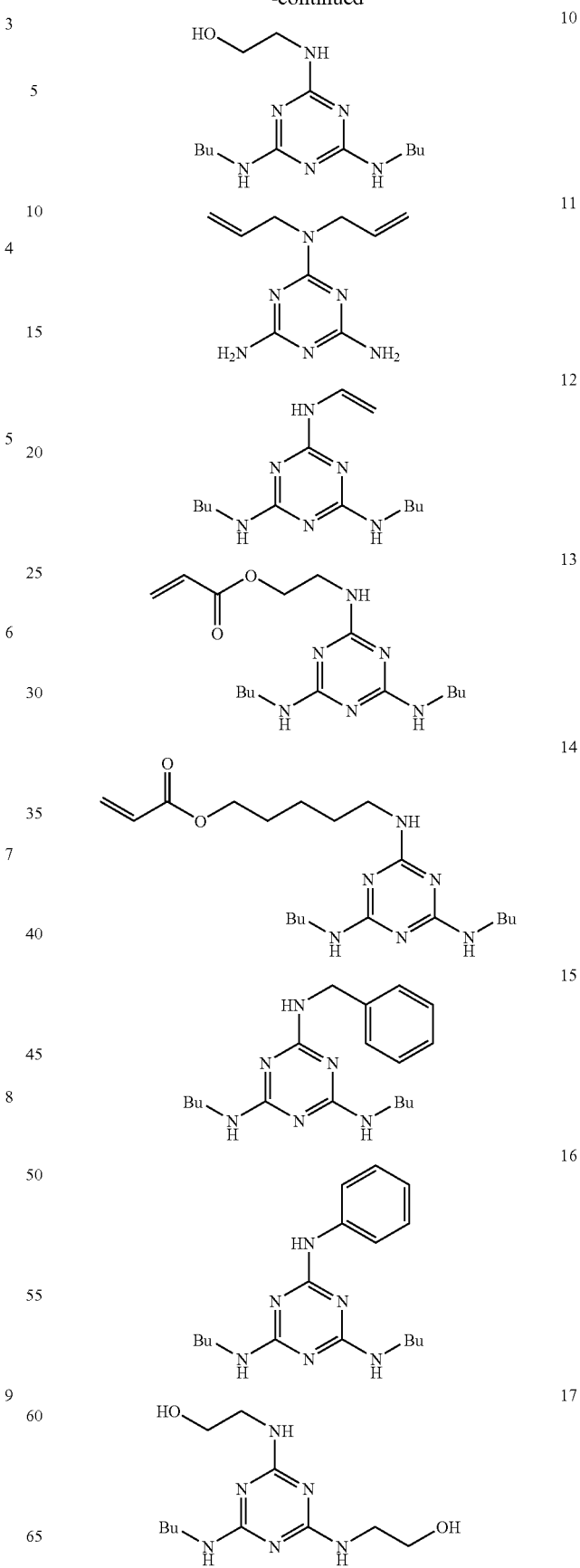

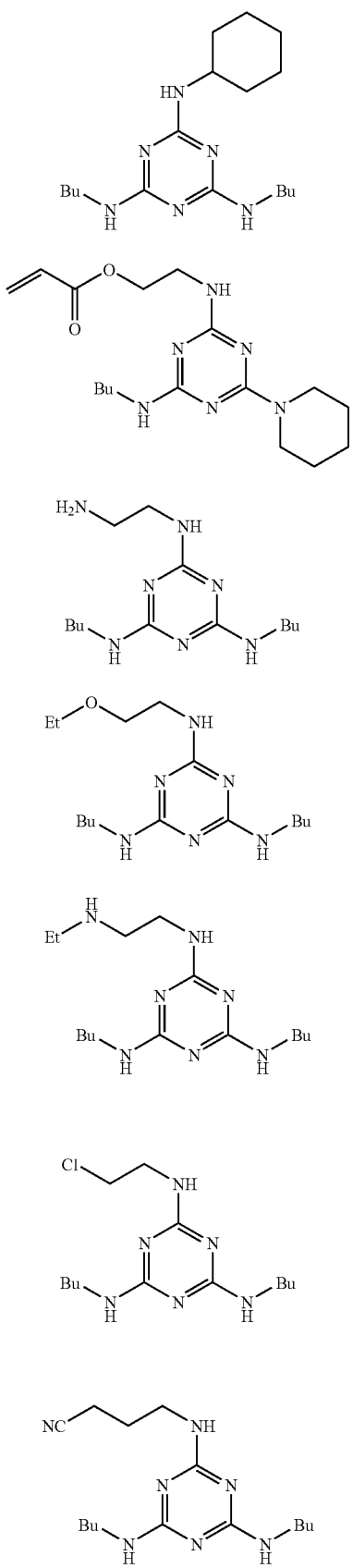

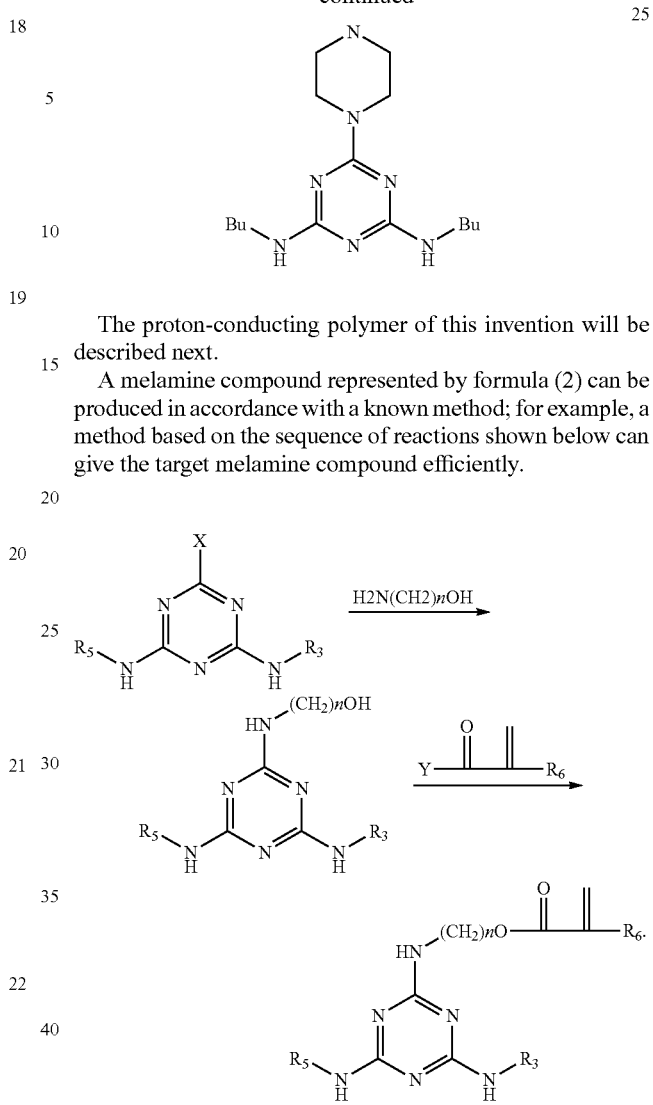

The proton-conducting polymer of this invention will be described next.

A melamine compound represented by formula (2) can be produced in accordance with a known method; for example, a method based on the sequence of reactions shown below can give the target melamine compound efficiently.

That is, a triazine compound represented by formula (3) is treated with an aminoalcohol in reaction 1 to give a melamine derivative represented by formula (4) and the said melamine derivative is then treated with an acrylic acid derivative in reaction 2 to give the target melamine compound.

In the aforementioned formulas, X is a halogen atom, $R_3$ and $R_5$ respectively have the same meaning as $R_3$ and $R_5$ in formula (2) and at least one of them is a group other than hydrogen. The aminoalcohol to be submitted to the reaction with the triazine compound may be any compound whose carbon chain has an amino group at one end and a hydroxyl group at the other and the number of carbon atoms in the chain is preferably 2 to 10. That is, n in formula (2) is preferably 2 to 10.

The aforementioned reaction 1 can be carried out without a catalyst, but it is made to proceed more smoothly in the presence of a base catalyst. The base catalyst is preferably an organic base and its examples include aliphatic tertiary amines such as triethylamine, triisopropylamine, and diisopropylethylamine. The organic base is used preferably in excess of the triazine compound represented by formula (3), normally 1.2 to 5 times that of the triazine compound on a molar basis.

Reaction 1 is normally carried out in the presence of a solvent. Any solvent that does not interfere with the reaction may be used and its examples include aliphatic hydrocarbons such as hexane, heptane, and petroleum ether, aromatic hydrocarbons such as benzene, toluene, and xylene, organic nitro compounds such as nitromethane and nitrobenzene, cyclic ethers such as tetrahydrofuran and dioxane, and the so-called aprotic polar solvents such as dimethylacetamide, dimethylformamide, dimethylimidazolidinone, sulfolane, and N-methylpyrrolidone.

The reaction temperature ranges normally from room temperature to 250° C., preferably from 100 to 200° C.

Upon completion of the reaction, the reaction mixture is processed in the usual manner to give a melamine derivative represented by formula (4). The said derivative is then subjected to reaction 2 wherein it is allowed to react with an acrylic acid derivative represented by formula (5) to give a melamine compound represented by formula (2). In formula (5), Y is an alkoxy group, a hydroxyl group, or a halogen atom and $R_5$ is hydrogen or an alkyl group. The alkoxy group here preferably contains 1 to 6 carbon atoms.

The aforementioned reaction 2 is carried out under the reaction conditions conforming to the kind of Y to give the target melamine compound represented by formula (2). For example, when Y is an alkoxy group, the melamine derivative represented by formula (4) is treated with an alkoxy group-containing acrylic acid derivative in a solvent in the presence of a base catalyst gives the target compound. Examples of the base catalyst include metal hydrides such as sodium hydride, calcium hydride, and potassium hydride, metallic sodium, metallic potassium, and sodium amide. The use of an alcohol-removing agent such as molecular sieves is desirable for smooth progress of the reaction. Any solvent that does not interfere with the reaction can be used and its examples include cyclic ethers such as tetrahydrofuran and dioxane, the so-called aprotic polar solvents such as dimethylacetamide, dimethylformamide, dimethylimidazolidinone, sulfolane, and N-methylpyrrolidone, and organic nitro compounds such as nitromethane and nitrobenzene.

Reaction 2 is normally carried out at a temperature in the range from −20° C. to 50° C., preferably from −20° C. to room temperature. The reaction is allowed to proceed for a prescribed period of time and the reaction mixture is processed in the usual manner to give a melamine compound represented by formula (2).

A polymer that provides the proton-conducting solid electrolyte of this invention is obtained by the polymerization of a melamine compound salt (it is referred to as a proton exchange material as it functions as such or referred to as an M-B). The use of a crosslinking agent in this reaction improves the heat stability and conductivity as it copolymerizes with a melamine compound to form a polymer network in the resulting polymer. In the case where a melamine compound represented by formula (2) has two or more unsaturated linkages, the M-B salt prepared therefrom can form a polymer network without the presence of a crosslinking agent. It is also possible to effect copolymerization with a monomer other than a crosslinking agent.

A monomer having two or more radically polymerizable functional groups that are also radically copolymerizable with the aforementioned melamine compound is used as a crosslinking agent. Monomers of this kind are used singly or as a mixture of two or more. Examples of the preferable crosslinking agents include N,N'-methylenebisacrylamide, 1,8-nonadiene, 1,13-tetradecadiene, 1,4-butanediol divinyl ether, tetraethylene glycol dimethacrylate, tetraethylene glycol diacrylate, triethylene glycol divinyl ether, diethylene glycol divinyl ether, diethylene glycol diacrylate, diethylene glycol dimethacrylate, polyethylene glycol diacrylate, 1,6-hexanediol diacrylate, neopentyl glycol diacrylate, tripropylene glycol diacrylate, polypropylene glycol diacrylate, trimethylolpropane trimethacrylate, trimethylolpropane triacrylate, tetramethylolmethane tetraacrylate, triethylene glycol dimethacrylate, polyethylene glycol dimethacrylate, 1,3-butylene glycol dimethacrylate, 1,6-hexanediol dimethacrylate, and neopentyl glycol dimethacrylate.

The crosslinking agent is used in an amount corresponding to 0.1 to 59 wt %, preferably 1 to 30 wt %, more preferably 2 to 10 wt %, of the sum of the aforementioned melamine compound salt and the crosslinking agent. An amount below the lower limit of this range yields a low degree of crosslinking and cannot give a self-supporting solid electrolyte. On the other hand, an amount exceeding the upper limit raises the degree of crosslinking and a drop of the conductivity becomes a problem.

The aforementioned polymerization can be performed according to any of the known methods such as radical polymerization, ionic polymerization, coordination polymerization, and addition polymerization. A preferred method is radical polymerization because of its operational simplicity, but is not limited thereto. The radical polymerization is performed by heating, by irradiation with a visible light or ultraviolet rays, or by irradiation with a radiation such as electron rays. It is possible to add a polymerization initiator if necessary.

Examples of the aforementioned polymerization initiators include azo compounds such as 2,2'-azobisisobutyronitrile and 2,2'-azobis(2,4-dimethylvaleronitrile) and peroxides such as benzoyl peroxide, dicumyl peroxide, and diisopropyl peroxycarbonate in the case of thermal polymerization and acetophenone, benzophenone, and 2,2-dimethoxy-2-phenylacetophenone in the case of photopolymerization.

In the case where the objective is to produce the aforementioned polymer or the proton-conducting solid electrolyte of this invention in the form of membrane by thermal polymerization, a number of methods can be used to achieve this objective. For example, a solution of a melamine compound salt and a crosslinking agent is prepared, a polymerization initiator is dissolved in the solution if necessary, the resulting solution is spread in a Petri dish and allowed to polymerize at 60 to 80° C. under reduced pressure or in an atmosphere of nitrogen, and the reaction mixture is dried to yield the target membrane. In the case of photopolymerization, the solution spread in a Petri dish is allowed to polymerize under irradiation with ultraviolet rays and then dried.

The proton-conducting solid electrolyte of this invention (also referred to as polymer solid electrolyte) may, be composed of only a polymer obtained by neutralizing a melamine compound represented by formula (2) with a Bronsted acid and polymerizing the resulting melamine compound salt or it may be composed of a material containing the said polymer. The polymer preferably has a molecular weight in the range of 5,000 to 500,000.

The proton-conducting compound or proton-conducting polymer of this invention serves as a proton exchange material or a proton-conducting solid electrolyte. The uses of such proton-conducting compounds or proton-conducting polymers are not specified, but their proton conductivity can be fully exploited when used as a proton exchange material or a proton-conducting solid electrolyte; hence a proton exchange material and a proton-conducting solid electrolyte have roughly the same meaning with the exception of the question whether the latter needs to be solid or not.

The proton-conducting solid electrolyte of this invention may be a polymeric gelling material in which an M-B salt or a proton-conducting polymer is held and it can be molded into a membrane which is suitable for use as a proton exchange membrane in a solid polymer electrolyte membrane fuel cell.

The proton-conducting solid electrolyte of this invention functions as a proton conductor. The uses of the proton exchange material of this invention include the aforementioned fuel cells, ion exchange membranes, and medical applications (sodium-proton exchange in biological membranes).

The proton-conducting solid electrolyte of this invention comprises the aforementioned proton-conducting compound or proton-conducting polymer, advantageously a proton-conducting polymer. The said polymer may be a homopolymer or a copolymer of a melamine compound salt. In the case of the latter, it is preferably a copolymer produced from the raw material monomer mixture containing 50 wt % or more of the melamine compound salt or a copolymer in which 50 wt % or more of the structural units originates from the melamine compound salt. The comonomer to be used for the production of a copolymer desirably has two or more polymerizable functional groups, preferably olefinic functional groups, and acts as a crosslinking agent. A comonomer capable of participating in a crosslinking reaction is called a crosslinking agent.

The aforementioned polymer functions as a proton-conducting solid electrolyte even by itself and may be composed of the polymer alone or of a material containing the polymer.

A polymer solid electrolyte comprising the proton-conducting polymer of this invention may be used in the form of a polymer composition containing a composite produced from the aforementioned polymer and another thermoplastic polymer. A number of methods are available for the production of such a composite. For example, a varnish is prepared by dissolving a polymer whose examples are described below, the aforementioned melamine compound salt, and a crosslinking agent in a solvent, spreading the varnish in a container such as a Petri dish or on a glass plate, allowing the varnish to polymerize, and drying the resulting composite product. The polymer here is not limited to any specific one and a polymer capable of producing a composite with the proton-conducting polymer can be used; examples of the polymer include vinyl polymers such as polyvinyl chloride, polyacrylonitrile, poly(methyl methacrylate), and polyvinylidene fluoride, polyethers such as polyoxymethylene, polyethylene oxide, and polypropylene oxide, polyamides such as nylon 6 and nylon 66, polyesters such as polyethylene terephthalate, polyimides, and polycarbonates.

The content of the aforementioned polymer in a proton-conducting solid electrolyte is 1 to 80 wt %, preferably 5 to 75 wt %. A content less than the lower limit does not produce sufficient proton conductivity while a content in excess of the upper limit does not produce a difference in properties between a composite product and a non-composite product.

A fuel cell employing the proton-conducting solid electrolyte of this invention is illustrated in FIG. 12. The fuel cell is constructed by inserting the proton-conducting solid electrolyte of this invention 5 between catalyst-coated carbon cloths 4 and 6 and putting this layered structure between separators 8 and 9. The fuel cell is fixed between a pair of terminal plates, each consisting of an inner copper terminal plate 3 and an outer stainless steel terminal plate 2. The stainless steel terminal plates 2 on both sides are clamped together by glass-insulated bolts 1. A set of inlet and outlet for a gas is provided on the fuel electrode side and another set on the oxygen electrode side, each penetrating the separator 8 or 9, the copper terminal plate 3, and the stainless steel terminal plate 3, and fuel gas and oxygen gas flow through them in contact with the electrodes.

BRIEF DESCRIPTION OF THE DRAWINGS

FIG. 1 is an NMR chart of the melamine compound obtained in Example 1.

FIG. 2 is an NMR chart of the melamine compound obtained in Example 2.

FIG. 3 is an NMR chart of the melamine compound obtained in Example 3.

FIG. 4 is an NMR chart of the melamine compound obtained in Example 4.

FIG. 5 is an NMR chart of the melamine compound obtained in Example 6.

FIG. 6 is an NMR chart of the melamine compound obtained in Example 8.

FIG. 7 is an NMR chart of the melamine compound obtained in Example 9.

FIG. 8 is an NMR chart of the melamine compound obtained in Example 14.

FIG. 9 is an NMR chart of the melamine compound obtained in Example 15.

FIG. 10 is a schematic diagram of an apparatus for evaluating the performance as a proton conductor.

FIG. 11 is a diagram showing the relationship between voltage and current when hydrogen or nitrogen is circulated.

FIG. 12 is the cross section of a fuel cell.

EXPLANATION OF SYMBOLS

2: Stainless steel terminal plate
3: Copper terminal plate
4, 6: Catalyst-coated carbon cloth
5: Electrolyte membrane
7: Loading apparatus
8, 9: Separator
11: Platinum electrode
12: Platinum electrode
13: Inlet of hydrogen gas

EXAMPLES

This invention will be described in detail below with reference to the accompanying examples.

The proton conductivity in the examples was determined by the AC impedance method at 160° C. without humidification.

Example 1

A solution of 150 millimoles of n-butylamine in 50 ml of dimethylacetamide was prepared and cooled to 0° C. To this solution was added at 0° C. a solution of 250 millimoles of diisopropylethylamine and 50 millimoles of N,N'-dibutyl-6-chloro-[1,3,5]triazine-2,4-diamine in 50 ml of dimethylacetamide, the resulting solution was heated under reflux for 4 hours, then cooled to room temperature, and the solvent was distilled off by an evaporator. The reaction mixture was then isolated and purified by silica gel column chromatography to give N,N',N"-tributyl-[1,3,5]triazine-2,4,6-triamine as an oily substance. The result of 1H-NMR analysis is shown in FIG. 1.

1H-NMR (CDCl3): 4.80 (br, 3h), 3.34 (br, 6h), 1.51 (m, 6h), 1.35 (m, 6h), 1.35 (m, 6h), 0.90 (m, 9h)

To a methanol solution of 10 millimoles of bis(trifluoromethanesulfonyl)imide was added 10 millimoles of N,N',N"-tributyl-[1,3,5]triazine-2,4,6-triamine and stirred at room temperature. After 30 minutes, the solvent was distilled off and the bis(trifluoromethanesulfonyl)imide salt of N,N',N"- tributyl-[1,3,5]triazine-2,4,6-triamine was obtained as an oily substance. The proton conductivity of this salt was determined by the AC impedance method to be 6 mS/cm at 150° C. without humidification.

Examples 2-6

The procedure of Example 1 was repeated with the exception of using n-octylamine, ethylpropylamine, pyrrolidine, morpholine, ethanolamine, or diethylamine in place of n-butylamine and the corresponding melamine compound obtained was converted to its bis(trifluoromethanesulfonyl)imide salt. The chemical formula of the melamine compound, appearance of the salt, and proton conductivity are shown in Table 1.

TABLE 1

| Example | Melamine compound | Appearance of salt at room temperature | Proton conductivity |
|---|---|---|---|
| 2 | 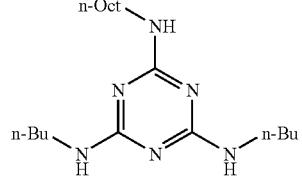 | oily | 3 mS/cm |
| 3 | 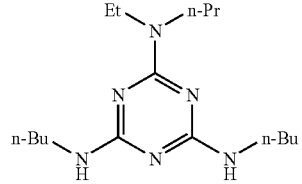 | oily | 7 mS/cm |
| 4 | 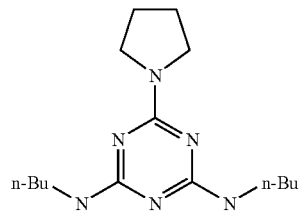 | oily | 6 mS/cm |
| 5 | 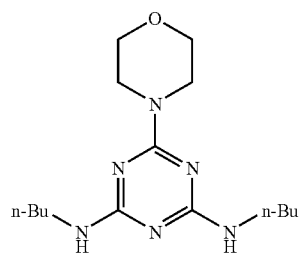 | oily | 5 mS/cm |

TABLE 1-continued

| Example | Melamine compound | Appearance of salt at room temperature | Proton conductivity |
|---|---|---|---|
| 6 | 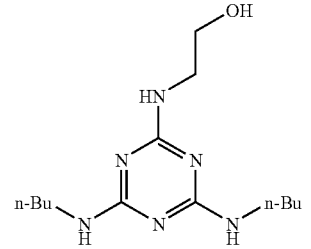 | oily | 5 mS/cm |
| 7 | 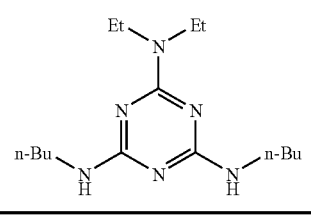 | oily | 7 mS/cm |

Example 8

A solution of 150 millimoles of n-butylamine in 50 ml of dimethylacetamide was prepared and cooled to 0° C. To this solution was added at 0° C. a solution of 250 millimoles of diisopropylethylamine and 50 millimoles of N,N'-diethyl-6-chloro-[1,3,5]triazine-2,4-diamine in 50 ml of dimethylacetamide, the resulting solution was heated under reflux for 4 hours, then cooled to room temperature, and the solvent was distilled off by an evaporator. The reaction mixture was then isolated and purified by silica gel column chromatography to give N,N-diethyl-N''-n-butyl-[1,3,5]triazine-2,4,6-triamine as an oily substance.

To a methanol solution of 10 millimoles of bis(trifluoromethanesulfonyl)imide was added 10 millimoles of N,N-diethyl-N''-n-butyl-[1,3,5]triazine-2,4,6-triamine and stirred at room temperature. After 30 minutes, the solvent was distilled off and the corresponding bis(trifluoromethanesulfonyl)imide salt was obtained as an oily substance. The proton conductivity of this salt was 10 mS/cm.

Example 9

A solution of 150 millimoles of n-octylamine in 50 ml of dimethylacetamide was prepared and cooled to 0° C. To this solution was added at 0° C. a solution of 250 millimoles of diisopropylethylamine and 50 millimoles of N-n-butyl-6-chloro-N'-ethyl-[1,3,5]triazine-2,4-diamine in 50 ml of dimethylacetamide, the resulting solution was heated under reflux for 4 hours, then cooled to room temperature, and the solvent was distilled off by an evaporator. The reaction mixture was then isolated and purified by silica gel column chromatography (hexane:AcOEt=1:1) to give N-n-butyl-N'-ethyl-N''-n-octyl-[1,3,5]triazine-2,4,6-triamine as an oily substance. To a methanol solution of 10 millimoles of bis(trifluoromethanesulfonyl)imide was added 10 mmoles of N-n-butyl-N'-ethyl-N''-n-octyl-[1,3,5]triazine-2,4,6-triamine and stirred at room temperature. After 30 minutes, the solvent was distilled off and the bis(trifluoromethanesulfonyl)imide salt of N-n-butyl-N'-ethyl-N''-n-octyl-[1,3,5]triazine-2,4,6-triamine was obtained as an oily substance. The proton conductivity of the salt was 4 mS/cm.

Example 10

The procedure of Example 9 was repeated with the exception of using pyrrolidine in place of n-octylamine to give the corresponding bis(trifluoromethanesulfonyl)imide salt. The proton conductivity of the salt was 5 mS/cm.

Example 11

To a methanol solution of 10 millimoles of bis(trifluoromethanesulfonyl)imide was added 10 millimoles of N,N-di-2-propenyl-[1,3,5]triazine-2,4,6-triamine and stirred at room temperature. After 30 minutes, the solvent was distilled off and the bis(trifluoromethanesulfonyl)imide salt of N,N-di-2-propenyl-[1,3,5]triazine-2,4,6-triamine was obtained. The proton conductivity of the salt was 7 mS/cm.

Example 12

The procedure of Experiment 1 was repeated with the exception of using 10 millimoles of phosphoric acid in place of 10 millimoles of bis(trifluoromethanesulfonyl)imide to give the phosphate salt of N,N',N''-tributyl-[1,3,5]triazine-2,4,6-triamine as an oily substance. The proton conductivity of the salt was 1 mS/cm.

Example 13

The procedure of Experiment 1 was repeated with the exception of using 10 millimoles of acetic acid in place of 10 millimoles of bis(trifluoromethanesulfonyl)imide to give the acetate salt of N,N',N''-tributyl-[1,3,5]triazine-2,4,6-triamine as an oily substance. The proton conductivity of the salt was 0.3 mS/cm.

Example 14

A solution of 162.7 millimoles of pyrrolidine in 75 ml of THF was cooled to 0° C., 81.3 millimoles of triazine trichloride, 244 millimoles of diisopropylethylamine, and 75 ml of THF were added to this solution, and the mixture was stirred at room temperature. After 17 hours, the solvent was distilled off and the residue was filtered to give the crystals of N,N'-bispyrrolidyl-6-chloro-[1,3,5]triazine-2,4-diamine. To the crystals were added 150 ml of dimethylacetamide, 250 millimoles of diisopropylethylamine, and 162.7 millimoles of n-butylamine and the mixture was heated under reflux. After 4 hours, the solvent was distilled off and the residue was purified by column chromatography (silica gel) to give N,N'-bispyrrolidyl-N''-n-butyl-[1,3,5]triazine-2,4,6-triamine as an oily substance.

To a solution of 10 millimoles of bis(trifluoromethanesulfonyl)imide was added millimoles of N,N'-bispyrrolidyl-N''-n-butyl-[1,3,5]triazine-2,4,6-triamine obtained above and stirred at room temperature. After 30 minutes, the solvent was distilled off and the bis(trifluoromethanesulfonyl)imide salt of N,N'-bispyrrolidyl-N''-n-butyl-[1,3,5]triazine-2,4,6-triamine was obtained as an oily substance. The proton conductivity of the salt was 10.7 mS/cm.

Example 15

The procedure of Example 8 was repeated with the exception of using pyrrolidine in place of n-butylamine to give the bis(trifluoromethanesulfonyl)imide salt of N,N'-diethyl-N''-pyrrolidyl-[1,3,5]triazine-2,4,6-triamine. The proton conductivity of the salt was 11 mS/cm.

Example 16

In 120 ml of THF was dissolved 10 millimoles of N,N'-dibutyl-N''-hydroxyethyl-[1,3,5]triazine-2,4,6-triamine obtained in Example 6 and sodium hydride was added to the solution. A solution of 20 millimoles of methyl methacrylate in 30 ml of THF was then added and stirred at room temperature. After 3 hours, the solvent was distilled off and the residue was purified by column chromatography (silica gel) to give the methacrylate ester of N,N'-dibutyl-N''-hydroxyethyl-[1,3,5]triazine-2,4,6-triamine as an oily substance.

To a methanol solution of 10 millimoles of bis(trifluoromethanesulfonyl)imide was added 10 millimoles of the methacrylate ester of N,N'-dibutyl-N''-hydroxyethyl-[1,3,5]triazine-2,4,6-triamine obtained above and stirred at room temperature. After 30 minutes, the solvent was distilled off and the bis(trifluoromethanesulfonyl)imide salt of the methacrylate ester of N,N'-dibutyl-N''-hydroxyethyl-[1,3,5]triazine-2,4,6-triamine was obtained as an oily substance. The proton conductivity of the salt was 4.7 mS/cm.

Example 17

As shown in FIG. 10, the bis(trifluoromethanesulfonyl)imide salt of N,N'-dibutyl-6-n-octyl-[1,3,5]triazine-2,4,6-triamine obtained in Example 2 was added to a U-shaped glass cell in which platinum electrodes 11 and 12 are provided at both ends and a gas bubbling tube 13 is provided on the side of the platinum electrode 11. Passage of an electric current was tested as follows; the cell was connected to a DC power source so that the electrode 1 became a positive electrode and the electrode 12 became a negative electrode and nitrogen or hydrogen was circulated through the gas bubbling tube 13. The test results are shown in FIG. 11.

When nitrogen was circulated through the gas bubbling tube 13, practically no passage of an electric current was observed as shown in FIG. 11. However, the current was proportional to the voltage during circulation of hydrogen. That is, the protons generated at the electrode 11 turn to hydrogen at the electrode 12 during circulation of hydrogen. This confirms that an M-B salt used as a proton-conducting compound according to this invention functions as a proton conductor.

Example 18

In a 500-ml eggplant-shaped flask were placed 77.8 millimoles of N,N'-dibutyl-6-chloro-[1,3,5]triazine-2,4-diamine, 100 ml of dimethylacetamide, 233.5 millimoles of diisopropylethylamine, and 155.6 millimoles of ethanolamine and the mixture was heated at 160° C. with stirring. After 1.5 hours, the mixture was cooled to room temperature and the solvent was distilled off. A white precipitate in the residue was filtered and the filtrate was purified by silica gel column chromatography to give N,N'-dibutyl-N''-hydroxyethyl-[1,3,5]triazine-2,4,6-triamine.

In a three-necked flask was placed 10 millimoles of N,N'-dibutyl-N''-hydroxyethyl-[1,3,5]triazine-2,4,6-triamine, the air in the flask was replaced with nitrogen, and 120.0 ml of dry THF was added to dissolve the compound. To the resulting solution was added 15.0 millimoles of sodium hydride and the mixture was stirred for 1 hour. The mixture was allowed to return to room temperature, 30 g of MS-5A (Molecular Sieves 1/16) was added, a solution of 20 millimoles of methyl methacrylate in 30 ml of THF was added from a dropping funnel over 30 minutes and the mixture was stirred for 3 hours. The MS-5A was removed by filtration and the solvent was distilled off by an evaporator. Water and dichloromethane were added to the remaining reaction mixture and the dichloromethane layer was concentrated. The concentrated reaction mixture was isolated and purified by silica gel column chromatography to give the methacrylate ester of N,N'-dibutyl-N''-hydroxyethyl-[1,3,5]triazine-2,4,6-triamine.

The sequence of reactions is shown below.

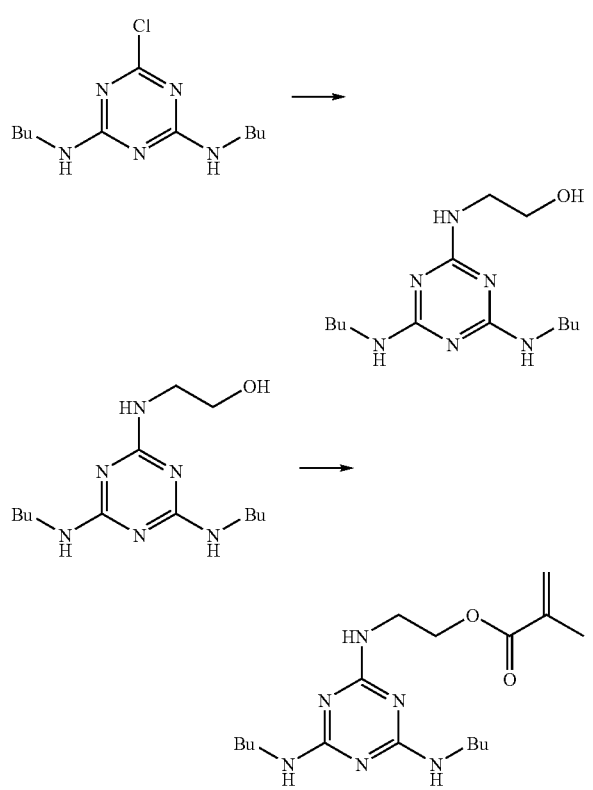

In dichloromethane was dissolved 4.86 millimoles of the methacrylate ester of N,N'-dibutyl-N''-hydroxyethyl-[1,3,5]triazine-2,4,6-triamine obtained above and to this solution was added dropwise a dichloromethane solution of 4.86 millimoles of bis(trifluoromethanesulfonyl)imide and stirred. After 3 hours, the solvent was distilled off and the residue was dried under reduced pressure to give the bis(trifluoromethanesulfonyl)imide salt of the methacrylate ester of N,N'-dibutyl-N''-hydroxyethyl-[1,3,5]triazine-2,4,6-triamine. The proton conductivity of this salt was measured by the AC impedance method without humidification. The results are shown in Table 2.

TABLE 2

| °C. | Conductivity (mS/cm) |
|---|---|
| 100 | 1.4 |
| 120 | 2.4 |
| 140 | 3.3 |
| 160 | 4.7 |

Example 19

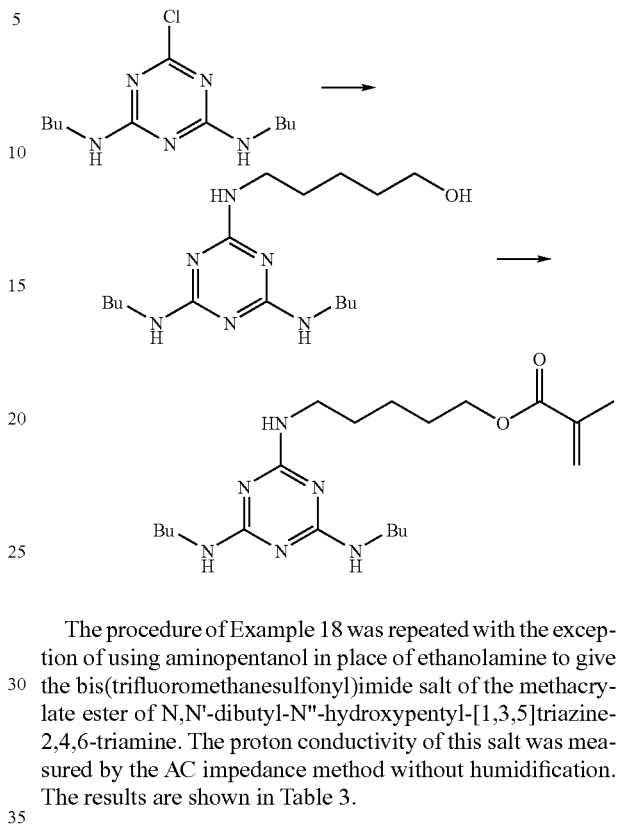

The procedure of Example 18 was repeated with the exception of using aminopentanol in place of ethanolamine to give the bis(trifluoromethanesulfonyl)imide salt of the methacrylate ester of N,N'-dibutyl-N''-hydroxypentyl-[1,3,5]triazine-2,4,6-triamine. The proton conductivity of this salt was measured by the AC impedance method without humidification. The results are shown in Table 3.

TABLE 3

| °C. | Conductivity (mS/cm) |
|---|---|
| 100 | 1.6 |
| 120 | 2.5 |
| 140 | 5.2 |
| 160 | 7.8 |

Example 20

In 3.5 ml of N-methylpyrrolidinone were dissolved 750 mg of the bis(trifluoromethanesulfonyl)imide salt of the methacrylate ester of N,N'-dibutyl-N''-hydroxypentyl-[1,3,5]triazine-2,4,6-triamine obtained in Example 18, 120 mg of tetraethylene glycol diacrylate, 2,2'-azobis(isobutyronitrile), and 250 mg of polyvinylidene fluoride. The resulting solution was spread in a Petri dish and left standing for 18 hours under reduced pressure at 60° C. The membrane formed was peeled off and tested for the proton conductivity by the AC impedance method without humidification. The results are shown in Table 4.

TABLE 4

| °C. | Conductivity (mS/cm) |
|---|---|
| 100 | 1.0 |
| 120 | 1.4 |
| 140 | 1.2 |
| 160 | 1.3 |

The presence of insoluble matters was confirmed in the membrane thus obtained when N-methylpyrrolidinone was added to the membrane and stirred at room temperature for 30 minutes. This finding indicates that the bis(trifluoromethanesulfonyl)imide salt of the methacrylate ester of N,N'-dibutyl-N"-hydroxyetyl-[1,3,5]triazine-2,4,6-triamine copolymerized with tetraethylene glycol diacrylate to form solvent-insoluble crosslinked products under the aforementioned film-forming conditions.

Example 21

In 3.5 ml of N-methylpyrrolidinone were dissolved 750 mg of the bis(trifluoromethanesulfonyl)imide salt of the methacrylate ester of N,N'-dibutyl-N"-hydroxypentyl-[1,3,5]triazine-2,4,6-triamine obtained in Example 19, 120 mg of tetraethylene glycol diacrylate, 2,2'-azobis(isobutyronitrile), and 250 mg of polyvinylidene fluoride. The resulting solution was spread in a Petri dish and left standing for 18 hours under reduced pressure at 60° C. The membrane formed was peeled off and tested for the proton conductivity by the AC impedance method without humidification. The results are shown in Table 5.

TABLE 5

| °C. | Conductivity (mS/cm) |
| --- | --- |
| 100 | 1.0 |
| 120 | 1.4 |
| 140 | 2.5 |
| 160 | 4.2 |

The presence of insoluble matters was confirmed in the membrane thus obtained when N-methylpyrrolidinone was added to the membrane and stirred at room temperature for 30 minutes. This finding indicates that the bis(trifluoromethanesulfonyl)imide salt of the methacrylate ester of N,N'-dibutyl-N"-hydroxypentyl-[1,3,5]triazine-2,4,6-triamine copolymerized with tetraethylene glycol diacrylate to form solvent-insoluble crosslinked products.

INDUSTRIAL APPLICABILITY

A proton-conducting compound or a proton-conducting polymer to be provided by this invention is useful as a proton exchange material and is suited for use as a material for electrochemical devices such as solid electrolytes for fuel cells and electrolytes for batteries where its ability to manifest proton conductivity without humidification, a property hitherto regarded difficult to obtain, can be fully exploited.

The invention claimed is:

1. A proton-conducting compound composed of a melamine compound salt obtained from a melamine compound represented by the following formula (1) and a Bronsted acid:

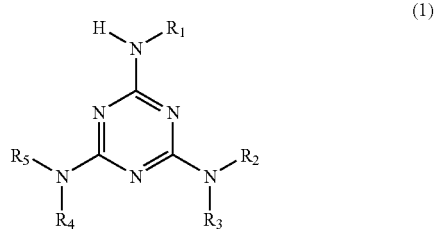

wherein:
$R_1$ is $CH_2=CR_6-CO-O(CH_2)_n-$;
$R_2$, $R_3$, $R_4$, and $R_5$ each is independently an alkyl group, an aryl group, a heterocyclic group, or hydrogen and at least one of them is an alkyl group, an aryl group, or a heterocyclic group; $R_2$ and $R_3$ or $R_4$ and $R_5$ may join together to form a heterocyclic structure;
$R_6$ is hydrogen or an alkyl group and n is an integer equal to or larger than 1; and
the alkyl group, the aryl group, and the heterocyclic group each may have a substituent selected from the group of alkyl groups of 1 to 6 carbon atoms, aryl groups of 6 to 12 carbon atoms, heterocyclic groups, an amino group, alkylamino groups of 1 to 6 carbon atoms, a nitro group, a carboxyl group, acyl groups of 1 to 6 carbon atoms, acyloxy groups of 1 to 6 carbon atoms, a cyano group, alkylsulfonyl groups of 1 to 6 carbon atoms, alkylsulfonyloxy groups of 1 to 6 carbon atoms, a sulfoxide group, a sulfonic acid group, alkoxycarbonyl groups of 1 to 6 carbon atoms, aryloxycarbonyl groups of 6 to 12 carbon atoms, aryloxy groups of 6 to 12 carbon atoms, and alkynyl groups of 2 to 6 carbon atoms;
and wherein the Bronsted acid is sulfuric acid, phosphoric acid, boric acid, a heteropolyacid, alkylsulfonic acid, a fluorine-containing alkylsulfonic acid, an alkylcarboxylic acid, or an imide acid, wherein the alkyl moiety contains 1 to 6 carbon atoms.

2. A proton-conducting compound as described in claim 1 wherein the said compound is composed of a melamine compound salt produced by the reaction of a melamine compound represented by formula (1) with a Bronsted acid in a ratio of 0.5 to 2 equivalents of Bronsted acid per 1 mole of melamine compound.

3. A proton-conducting solid electrolyte comprising the proton-conducting compound described in claim 1.

4. A proton-conducting solid electrolyte as described in claim 3 wherein the proton-conducting compound is held in a polymeric gelling material.

5. A proton-conducting solid electrolyte membrane formed by molding the proton-conducting solid electrolyte described in claim 4 into membrane.

6. An electrolyte for electrochemical cells comprising the proton-conducting solid electrolyte described in claim 3.

7. A fuel cell comprising the electrolyte for electrochemical cells described in claim 6.

8. A fuel cell comprising the proton-conducting solid electrolyte membrane described in claim 5.

* * * * *